(12) United States Patent
Resconi et al.

(10) Patent No.: US 7,314,903 B2
(45) Date of Patent: Jan. 1, 2008

(54) CATALYST SYSTEM FOR THE POLYMERIZATION OF OLEFINS

(75) Inventors: Luigi Resconi, Ferrara (IT); Francesca Focante, Filottrano (IT); Isabella Camurati, Ferrara (IT); Simona Guidotti, Altedo-Malalbergo (IT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/520,565

(22) PCT Filed: Jul. 9, 2003

(86) PCT No.: PCT/EP03/07485

§ 371 (c)(1),
(2), (4) Date: Jan. 7, 2005

(87) PCT Pub. No.: WO2004/005360

PCT Pub. Date: Jan. 15, 2004

(65) Prior Publication Data

US 2006/0094840 A1    May 4, 2006

Related U.S. Application Data

(60) Provisional application No. 60/394,614, filed on Jul. 9, 2002.

(51) Int. Cl.
*C08F 6/64* (2006.01)
*C08F 6/643* (2006.01)
*C08F 6/6392* (2006.01)
*C08F 4/70* (2006.01)

(52) U.S. Cl. .................. 526/134; 526/133; 526/160; 526/161; 526/172; 526/139; 526/141; 502/103; 502/123; 502/167; 502/152

(58) Field of Classification Search ............... 526/133, 526/134, 160, 161, 172, 139, 141; 502/103, 502/123, 167, 152
See application file for complete search history.

(56) References Cited

U.S. PATENT DOCUMENTS 6,608,224 B2 * 8/2003 Resconi et al. ............... 556/27

FOREIGN PATENT DOCUMENTS

| EP | 0416815 | 3/1991 |
|---|---|---|
| EP | 0420436 | 4/1991 |
| EP | 0643066 | 3/1995 |
| EP | 0671404 | 9/1995 |
| JP | 43029756 | 12/1968 |
| JP | 44006828 | 3/1969 |
| JP | 44013148 | 6/1969 |
| WO | 9102012 | 2/1991 |
| WO | 9104257 | 4/1991 |
| WO | 9623010 | 8/1996 |
| WO | 9627439 | 9/1996 |
| WO | 9702298 | 1/1997 |
| WO | 9840374 | 9/1998 |
| WO | 9921899 | 5/1999 |
| WO | 9964476 | 12/1999 |
| WO | 0162764 | 8/2001 |

OTHER PUBLICATIONS

B. Temme et al., "Oxidative $\eta^2$-iminoacyl formation by reaction of amidozirconocene complexes with tris(pentafluorophenyl)borane," *Journal of Organometallic Chemistry*, vol. 488, p. 177-182 (1995).
M. Brookhart et al., "Highly Active Iron and Cobalt Catalysts for the Polymerization of Ethylene," *J. Am. Chem. Soc.*, vol. 120, p. 4049-4050 (1998).
M. Brookhart et al., "New Pd(II)- and Ni(II)-Based Catalysts for Polymerization of Ethylene and α-Olefins," *J. Am. Chem. Soc.*, vol. 117(23), p. 6414-6415 (1995).
M. Brookhart et al,. "Copolymerization of Ethylene and Propylene with Functionalized Vinyl Monomers by Palladium(II) Catalysts," *J. Am. Chem. Soc.*, vol. 118, p. 267-268 (1996).
V. Gibson et al., "Novel olefin polymerization catalysts based on iron and cobalt," *Chem. Commun.*, p. 849-851 (1998).
H. W. Roesky et al., "Metallacyclodisiladiazanes of Titanium and Zirconium; Synthesis, Structure and Polymerization Studies," *Chem. Ber./Recueil*, vol. 130, p. 399-403 (1997).
Bernd Wrackmeyer et al., "Nuclear magnetic resonance studies on boron compounds, X. Boron-11, nitrogen-14 and proton NMR studies on boryl-substituted thiophene, furan, and N-methylpyrrole and related systems: interaction of sp2-boron atoms with pi-systems," *Chemische Berichte*, vol. 109(3), p. 1075-1088 (1976).
Database Caplus, Chemical Abstracts Service, Columbus, Ohio, Tadami Kamaishi et al., "Polymerization of alpha-olefin," (XP002264600) Database accession No. 71:92059 (abstract).
Database Caplus, Chemical Abstracts Service, Columbus, Ohio, Tadami Kamaishi et al., "Polypropylene," (XP002264601) Database accession No. 70:88432 (abstract).
Database Caplus, Chemical Abstracts Service, Columbus, Ohio, Tadami Kamaishi et al., "Crystalline polyolefins," (XP002264602) Database accession No. 71:22482 (abstract).

\* cited by examiner

*Primary Examiner*—Caixia Lu
(74) *Attorney, Agent, or Firm*—Jarrod N Raphael

(57) ABSTRACT

An organometallic compound obtainable by contacting: a compound having the following formula (I), wherein: $R^a$ is a hydrocarbon radical; $R^b$, $R^c$ and $R^d$, are hydrogen atoms, halogen atoms, or hydrocarbon radicals; with a Lewis acid of formula (II) $MtR^1_3$ (II) wherein Mt is a metal belonging to Group 13 of the Periodic Table of the Elements; $R^1$ are selected from the group consisting of halogen atoms, halogenated $C_6$–$C_{20}$ aryl and halogenated $C_7$–$C_{20}$ alkylaryl groups (I)

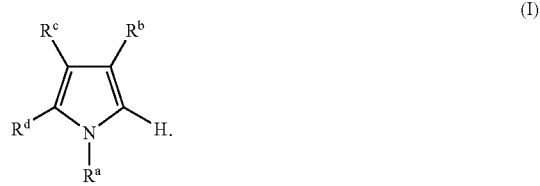

20 Claims, No Drawings

CATALYST SYSTEM FOR THE POLYMERIZATION OF OLEFINS

This application is the U.S. national phase of International Application PCT/EP2003/007485, filed Jul. 9, 2003, claiming the benefit under 35 U.S.C. 119(e) of U.S. Provisional Application No. 60/394,614, filed Jul. 9, 2002; the disclosures of International Application PCT/EP2003/007485, and U.S. Provisional Application No. 60/394,614, each as filed, are incorporated herein by reference.

The present invention relates to organometallic compounds, to catalyst systems for the polymerization of olefins comprising such organometallic compounds and to a process for the polymerization of olefins carried out in the presence of the above catalyst system. Homogeneous catalytic systems based on metallocene complexes are known to be active in the polymerization of olefins; said complexes must be activated by means of suitable cocatalytic compounds.

The first generation of cocatalysts developed for homogeneous metallocene olefin polymerization consisted of alkyl aluminum chlorides ($AlR_2Cl$), wherein substituents R are preferably methyl or ethyl; these cocatalysts exhibit low ethylene polymerization activity levels and negligible propylene polymerization activity.

The second generation of cocatalysts comprised the class of alkylalumoxanes, commonly obtained by reacting trialkyl aluminum compound and water in a molar ratio of 1:1 to 100:1; these alumoxanes are oligomeric linear and/or cyclic compounds represented by the formulae:

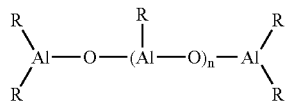

for linear oligomeric alumoxanes, and

for cyclic oligomeric alumoxanes, wherein the substituents R are usually methyl, ethyl or isobutyl groups, n ranges from 0 to 40, and m ranges from 3 to 40. Methylalumoxane (MAO) is the most widely used cocatalyst.

Nevertheless alkylalumoxanes, and in particular methylalumoxane, though very active in metallocene-based catalyst systems, exhibit several inherent problems in use, such as the need for high alumoxane/metallocene molar ratios to produce satisfactory catalytic activities, their high reactivity toward impurities (moisture, alcohols etc.) and their easy flammability. Moreover, it has not been possible to isolate characterizable metallocene active species using MAO. Accordingly, some of the developments in this area involved a search for alternative cocatalysts.

$B(C_6F_5)_4^-$ types of non-coordinating anions have been developed as cocatalysts for metallocene-based systems. More specifically, these activators are ion-exchange compounds comprising a trialkyl or dialkylammonium cation, which will irreversibly react with a metallocene, and a fluorinated arylborate anion, capable of stabilizing the metallocene cation complex and sufficiently labile to permit displacement by ethylene during polymerization (see for instance WO 91/02012). In particular, they have the advantage of being used in a 1:1 catalyst-cocatalyst ratio. Therefore, it is usually not necessary to remove the small amount of boron from the final polymer, unlike the aluminum-based cocatalysts mentioned above. As preferred activators are tri(n-butyl)ammonium tetrakis(pentafluorophenyl)boron and N,N-dimethylanilinium tetrakis(pentafluorophenyl)boron.

These cocatalysts exhibit high activities but, from a synthetic point of view, the industrial production of these cocatalysts is quite expensive.

Finally, these $B(C_6F_5)_4^-$ anions are generally used in the form of the corresponding ammonium salts, thus leading to the release of aminic by-products in consequence of the metallocene activation. In addition they have low solubility in polymerization solvents The fourth generation of cocatalysts is $B(C_6F_5)_3$. The anion $MeB(C_6F_5)_3^-$ formed after $Me^-$ abstraction from the metallocene dimethyl complex is weakly coordinated to the electrondeficient metal center, thus resulting in a decrease of the catalytic activity and in addition the catalyst system is not stable.

An alternative route for using $B(C_6F_5)_3$ has been proposed by B. Temme in Journal of Organometallic Chemistry, 488 (1995), 177–182. Biscyclopentadienyl-methyl-pyrrolidyl zirconocene has been treated with $B(C_6F_5)_3$ with the formation of the pyrrolydyl borate and the metallocene cation. In this paper it is reported that the obtained salt is catalytically active and polymerizes ethylene even if with a moderate activity.

WO 99/64476 describes a process for the preparation of polyolefins by using a catalyst system comprising a metallocene compound, a Lewis acid-base complex and a tri-n-alkylaluminum compound. As described at page 4 and illustrated in the figures, the function of the Lewis base is to inhibit the reaction between the metallocene compounds and the Lewis acid. Only upon addition of the tri-n-alkylaluminum compound the catalyst system becomes active. This catalyst system does not solve completely the problems of the use $B(C_6F_5)_3$, for the reason that the anion that is weakly coordinated to the electrondeficient metal center is always of the type $MeB(C_6F_5)_3^-$ and therefore the active catalyst system is not stable for a long time.

The recently published WO 01/62764 describes a new class of cocatalysts obtainable by contacting a N—H pyrrole derivative with a Lewis acid. The catalyst system comprising these cocatalyts and a metallocene compound can be isolated and identified.

Thus there is still the need to find a new cocatalyst which reduces the use of excess of cocatalyst with respect to alkylaluminoxanes, does not lead to the release of undesired by-products after the metallocene activation, and provides stable catalytic compositions.

The present invention concerns an organometallic compound obtainable by contacting:

a) a compound having the following formula (I):

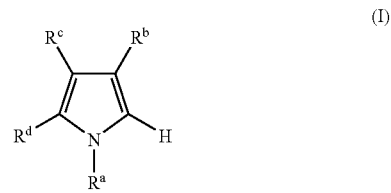

wherein:

$R^a$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^a$ can join $R^d$ to form a $C_4$–$C_7$ ring;

preferably $R^a$ is a $C_1$–$C_{10}$ alkyl, or $C_6$–$C_{20}$ aryl group; more preferably $R^a$ is methyl, ethyl, propyl, phenyl or a naphtyl group.

$R^b$, $R^c$ and $R^d$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^b$, $R^c$, and $R^d$ form one or more $C_4$–$C_7$ rings, optionally containing O, S, N, P or Si atoms, that can bear substituents; with b) a Lewis acid of formula (I)

$$MtR^1{}_3 \qquad (II)$$

wherein Mt is a metal belonging to Group 13 of the Periodic Table of the Elements (IUPAC); $R^1$, equal to or different from each other, are halogen atoms, halogenated $C_6$–$C_{20}$ aryl and halogenated $C_7$–$C_{20}$ alkylaryl groups; two $R^1$ groups can also form with the metal Mt one condensed ring, such as for example 9-borafluorene compounds.

Preferably Mt is B or Al, and more preferably is B; the substituents $R^1$ are $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl; most preferred $R^1$ substituents are $C_6F_5$ radicals.

Preferred organometallic compounds are those belonging to the following two classes (1) and (2), having respectively formula (III) and (IV).

Class (1)

Organometallic compounds belonging to class (1) have the following formula (III)

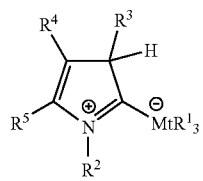

(III)

wherein

Mt is a metal belonging to Group 13 of the Periodic Table of the Elements (IUPAC); $R^1$, equal to or different from each other, are halogen atoms, halogenated $C_6$–$C_{20}$ aryl or halogenated $C_7$–$C_{20}$ alkylaryl groups; or two $R^1$ groups can form with the metal Mt one condensed ring, such as for example 9-borafluorene compounds; the substituents $R^5$, $R^4$ and $R^3$ equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^3$, $R^4$ and $R^5$ form one or more $C_4$–$C_7$ rings, optionally containing O, S, N, P or Si; preferably $R^4$ and $R^5$ form one condensed $C_5$–$C_6$ aromatic ring, optionally containing O, S, N, or P atoms, that replace one or more carbons of the aromatic ring and can bear substituents; preferably $R^3$ is hydrogen;

$R^2$ is a linear or branched, saturated or unsaturated, $C_1$–$C_{10}$ allyl, $C_6$–$C_{20}$ aryl, $C_7$–$C_{20}$ arylalkyl or $C_7$–$C_{20}$ alkylaryl group, optionally containing O, S, N, P, Si or halogen atoms or $R^2$ can join $R^5$ to form a $C_4$–$C_7$ ring; preferably $R^2$ is a $C_1$–$C_{10}$ alkyl, or $C_6$–$C_{20}$ aryl group; more preferably $R^2$ is methyl, ethyl, propyl, phenyl or a naphtyl group.

Preferably in the organometallic compounds of formula (III) Mt is B or Al, and more preferably is B; the substituents $R^1$ equal to or different from each other, $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl; even more preferably, $R^1$ is $C_6F_5$.

A preferred subclass of organometallic compounds of formula (III) is that of formula (V):

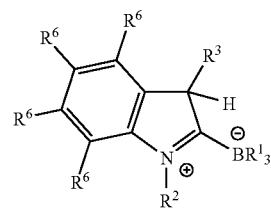

(V)

wherein

B is a boron atom;

the substituents $R^1$, $R^2$ and $R^3$ have the meaning reported above and the substituents $R^6$, the same or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups optionally containing O, S, N, P, Si or halogen atoms, or two or more adjacent substituents $R^6$ form one or more $C_4$–$C_7$ rings, optionally containing O, S, N, P or Si atoms that can bear substituents; preferably, $R^6$ are selected from the group consisting of hydrogen atoms, halogen atoms, and linear or branched, saturated or unsaturated $C_1$–$C_{10}$ alkyl.

Class (2)

Organometallic compounds belonging to class (2) have the following formula (IV):

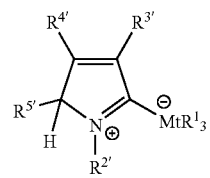

(IV)

wherein

Mt and $R^1$ are defined as above;

the substituents $R^{3'}$, $R^{4'}$ and $R^{5'}$ equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^{3'}$, $R^{4'}$ and $R^{5'}$ form one or more $C_4$–$C_7$ rings optionally containing O, S, N, P or Si atoms, that can bear substituents; said rings can be aliphatic or optionally can contain double bonds;

$R^{2'}$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^{2'}$ can join $R^{5'}$ to form a $C_4$–$C_7$ ring; preferably $R^{2'}$ is a $C_1$–$C_{10}$ alkyl, or $C_6$–$C_{20}$ aryl group; more preferably $R^{2'}$ is methyl, ethyl, propyl, tertbutyl, phenyl or a naphtyl group.

Preferably the substituents $R^{3'}$, $R^{4'}$ and $R^{5'}$, are hydrogen atoms, linear or branched, saturated or unsaturated, $C_1$–$C_{10}$ alkyl, optionally containing O, S, N, P, Si or halogen atoms, or two or more adjacent substituents $R^{3'}$, $R^{4'}$ and $R^{5'}$ form one or more $C_4$–$C_7$ rings optionally containing O, S, N, P or Si atoms, that can bear substituents; said rings can be aliphatic or optionally can contains double bonds, with the proviso that said rings are not aromatic.

A preferred subclass of organometallic compounds of formula (IV) is that of formula (VI):

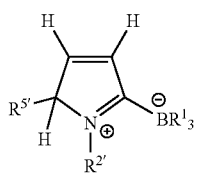

(VI)

wherein
the substituents $R^1$ and $R^{2'}$ have the meaning described above and the substituent $R^{5'}$ is a $C_1$–$C_{10}$ alkyl group; preferably $R^{5'}$ is a methyl or ethyl group.

The organometallic compounds of the invention are easily prepared by reacting, in about stoichiometric amounts, a compound having the formula (I):

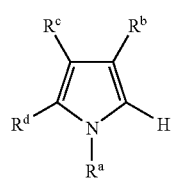

(I)

wherein $R^a$, $R^b$, $R^c$ $R^d$ and $R^e$ are described above; with a Lewis acid of formula (II)

$$MtR^1_3 \quad (II)$$

wherein Mt and $R^1$ are described above.

The reaction between said Lewis acid and the compound of formula (I) is preferably carried out in an aprotic solvent, even more preferably in a polar aprotic solvent (such as toluene, diethyl ether or $CH_2Cl_2$), at room temperature, the reaction can be carried out also in the presence of a small amount of water, preferably less than one molar equivalent with respect to the Lewis acid.

A further object of the present invention is a salt obtainable by contacting, in any order:
a) a compound having formula (I) as described above;
b) a Lewis acid of formula (II) as described above; and
c) a compound of formula $KR^f_3$ wherein K is a nitrogen (N) or phosphorous (P) atom; preferably K is nitrogen; $R^f$, equal to or different from each other, are linear or branched, saturated or unsaturated, $C_1$–$C_{30}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two $R^f$ can form one $C_4$–$C_7$ ring, optionally containing O, S, N, P or Si atoms, that can bear substituents; preferably $R^f$ is selected from the group consisting of linear or branched, saturated or unsaturated, $C_1$–$C_{30}$ alkyl.

This salt can be used as cocatalyst for the polymerization of olefins.

Preferred salts compounds are those belonging to the following two classes (3) and (4), having respectively formulas (VII) and (VIII).

Class (3)
Salts belonging to class (3) have formula (VI):

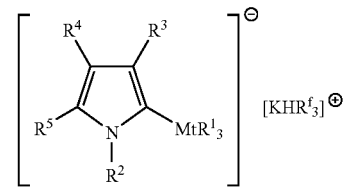

(VII)

wherein $R^1$, $R^2$, $R^3$, $R^4$, $R^5$, Mt, K and $R^f$ have the meaning described above.

A preferred subclass of salts of formula (VII) is that of formula (IX):

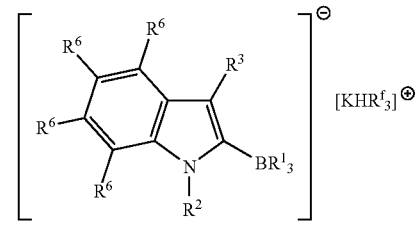

(IX)

wherein $R^1$, $R^2$, $R^3$, $R^6$, B, K and $R^f$ have the meaning described above.

Class (4)
Salts belonging to class (4) have formula (VIII):

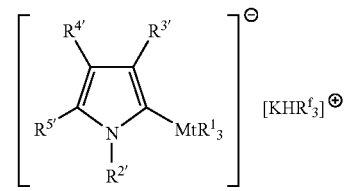

(VIII)

wherein $R^1$, $R^{2'}$, $R^{3'}$, $R^{4'}$, $R^{5'}$, Mt, K and $R^f$ have the meaning described above.

A preferred subclass of salts of formula (VIII) is that of formula (X):

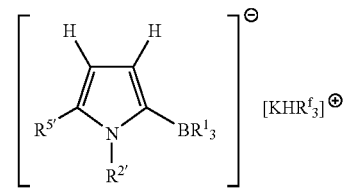

(X)

wherein $R^1$, $R^{2'}$, $R^{5'}$, Mt, K and $R^f$ have the meaning described above.

A process for preparing the above described salts comprises the following steps:
a) contacting at least one equivalent of a compound of formula (I) with one equivalent of a Lewis acid of formula (II), wherein the compound of formula (I) and (II) has been described above; and
b) optionally isolating the reaction product of step a) and then adding at least one equivalent of a compound of formula $KR^f_3$, wherein K and $R^f$ have been described above.

The two steps described above can be carried out both by isolating the intermediate product formed in step a), generally by filtration or evaporation of the solvent, or carried out "one pot" without isolating the intermediate product; preferably the reaction is carried out in an aprotic solvent, even more preferably in a polar aprotic solvent (such as toluene, diethyl ether or $CH_2Cl_2$), at room temperature. The reaction can be carried out also in the presence of little amount of water, preferably equal to or less than one molar equivalent with respect to the Lewis acid. The final product is generally isolated by filtration or evaporation of the solvent. An alternative process for preparing the above described salts comprises the step of contacting a compound of formula (III), (IV), (V) or (VI) with at least one equivalent of a compound of formula $KR^f_3$, wherein K and $R^f$ have been described above.

Non limitative examples of compounds belonging to formula (I) are:
N-methyl-pyrrole; N-methyl-2-ethylpyrrole; N-methyl-2,4-dimethylpyrrole; N-methyl-4,5,6,7-tetrahydroindole; N-methyl-2,4-dimethyl-3-ethylpyrrole; N-methyl-indole; N-methyl-3-methylindole; N-methyl-4-methylindole; N-methyl-5-methylindole; N-methyl-6-methylindole; N-methyl-7-methylindole; N-methyl-5-fluoroindole; N-methyl-4-chloroindole; N-methyl-5-chloroindole; N-methyl-6-chloroindole; N-methyl-5-bromoindole; N-methyl-5-methoxyindole; N-methyl-4-methoxyindole; N-methyl-5,6-dimethoxyindole; N-methyl-5-benzyloxy-indole; and the corresponding N-ethyl, N-propyl, N-phenyl and N-naphtyl compounds.

Example of Lewis acid of formula (II) are:
tris(pentafluorophenyl)borane; tris(heptafluoronaphthyl)borane; tris(2,3,5,6,7,8-hexafluoronaphthyl)borane; tris(2,4,5,6,7,8-hexafluoronaphthyl)borane; tris(3,4,5,6,7,8-hexafluoronaphthyl)borane; tris(2,3,4,6,7,8-hexafluoronaphthyl)borane; tris(2,3,4,5,7,8-hexafluoronaphthyl)borane; tris(2,3,5,6,7,8-hexafluoro-4-methylnaphthyl)borane; tris(2,4,5,6,7,8-hexafluoro-3-methylnaphthyl)borane; tris(3,4,5,6,7,8-hexafluoro-2-methylnaphthyl)borane; tris(2,3,4,6,7,8-hexafluoro-5-methylnaphthyl)borane; tris(2,3,4,5,7,8-hexafluoro-6-methylnaphthyl)borane; tris(nonafluorobiphenyl)borane; tris(2,2',3,3',5,5',6,6'-octafluorobiphenyl)borane; tris(3,3',4,4',5,5',6,6'-octafluorobiphenyl)borane; tris(2,2',4,4',5,5',6,6'-octafluorobiphenyl)borane; tris(2,2',3,3',4,4',6,6'-octafluorobiphenyl)borane; tris(2,2',3,3',4,4',5,5'-octafluorobiphenyl)borane; tris(2,2',3,3',5,5',6,6'-octafluorobiphenyl)borane; tris(3,3',4,4',5,5',6,6'-octafluorobiphenyl)borane; tris(2,2',4,4',5,5',6,6'-octafluorobiphenyl)borane; tris(2,2',3,3',4,4',6,6'-octafluoro-5,5'-methylbiphenyl)borane; tris(2,2',3,3',4,4',5,5'-octafluoro-6,6'-methylbiphenyl)borane; tris(2,2',3,3',5,5',6,6'-octafluoro-4,4'-biphenyl)borane; tris(3,3',4,4',5,5',6,6'-octafluoro-2,2'-biphenyl)borane; tris(2,2',4,4',5,5',6,6'-octafluoro-3,3'-biphenyl)borane; tris(2,3,4,6-tetrafluorophenyl)borane; tris(2,3,5,6-tetrafluorophenyl)borane; tris(2,3,5-trifluorophenyl)borane, tris(2,3,6-trifluorophenyl)borane; tris(1,3-difluorophenyl)borane, tris(2,3,5,6-tetrafluoro-4-methylphenyl)borane; tris(2,3,4,6-tetrafluoro-5-methylphenyl)borane; tris(2,6-difluoro-3-methylphenyl)borane; tris(2,4-difluoro-5-methylphenyl)borane; tris(3,5-difluoro-2-methylphenyl)borane; fluorobis(pentafluorophenyl)borane; chlorobis(pentafluorophenyl)borane; dichloro(pentafluorophenyl)borane; difluoro(pentafluorophenyl)borane; 9-chloro-9-boroperfluorofluorene; 9-methyl-9-boroperfluorpfluorene; 9-pentafluorophenyl-9-boroperfluorofluorene and 9-bromo-9-boroperfluorofluorene.

It is another object of the present invention a catalyst system for the polymerization of olefins comprising the product obtained by contacting:
(A) at least one transition metal organometallic compound, and,
(B) an organometallic compound obtainable by contacting
a) a compound having the following formula (I):

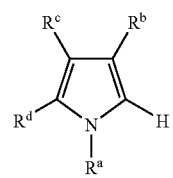

wherein $R^a$, $R^b$, $R^c$ and $R^d$ have the meaning described above
b) a Lewis acid of formula (II)

$$MtR^1_3 \quad (II);$$

wherein Mt and $R^1$ have the meaning described above; and
c) optionally a compound of formula $KR^f_3$, wherein K and $R^f$ have the meaning described above.

The catalyst system can optionally further comprise an alkylating agent.

Preferably the catalyst system of the present invention of olefins comprises the product obtained by contacting:
(A) at least one transition metal organometallic compound;
(B) an organometallic compound belonging to class (1) (compounds of formula (III), or (V)) or class (2) (compounds of formula (IV) or (VI)) as described above or a salt belonging to class (3) (salts of formula (VII) or (IX)) or class (4) (salts of formula (VIII) or (X)).

The catalyst system can optionally further comprise an alkylating agent.

Transition metal organometallic compounds for use in the catalyst system in accordance with the present invention are compounds suitable as olefin polymerization catalysts by coordination or insertion polymerization. The class includes known transition metal compounds useful in traditional Ziegler-Natta coordination polymerization, metallocene compounds and the transition metal compounds known to be useful in coordination polymerization. These typically include Group 4–10 transition metal compounds wherein at least one metal ligand can be abstracted by the catalyst activators. As a rule, when said ligand is hydrogen or an hydrocarbyl group containing from 1 to 20 carbon atoms optionally containing silicon atoms, the transition metal organometallic catalyst compounds can be used as such, otherwise an alkylating agent has to be used in order to alkylate said catalyst. The alkylation can be carried out in a separate step or in situ.

The alkylating agent is a compound able to react with the transition metal organometallic catalyst compounds and exchange said ligand that can be abstracted, with an alkyl group. Preferably said alkylating agent is selected from the group consisting of $R^{10}Li$, $R^{10}Na$, $R^{10}K$, $R^{10}MgU$ or $AlR^{10}{}_{3-z}W_z$, or alumoxanes, wherein $R^{10}$ can be $C_1$–$C_{10}$ alkyl, alkenyl or alkylaryl radicals, optionally containing one or more Si or Ge atoms, z is 0, 1 or 2 or a non integer number ranging from 0 to 2; U is chlorine, bromine or iodine and W is hydrogen, chlorine, bromine or iodine atom; non-limiting examples of $R^{10}$ are methyl, ethyl, butyl and benzyl; non limiting example of $AlR^{10}{}_{3-z}W_z$ compounds are trimethylaluminum (TMA), tris(2,4,4-trimethyl-pentyl) aluminum (TIOA), tris(2-methyl-propyl)aluminum (TIBA), tris(2,3,3-trimethyl-butyl)aluminum, tris(2,3-dimethyl-hexyl)aluminum, tris(2,3-dimethyl-butyl)aluminum, tris(2,3-dimethyl-pentyl)aluminum, tris(2,3-dimethyl-heptyl)aluminum, tris(2-methyl-3-ethyl-pentyl)aluminum and tris(2-ethyl-3,3-dimethylbutyl). Non limiting example of alumoxanes are: methylalumoxane (MAO), tetra-(isobutyl) alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Different from the catalyst system disclosed in WO 99/64476, the catalyst system of the present invention is stable and can be isolated.

A preferred class of transition metal organometallic compounds are metallocene compounds belonging to the following formula (XI)

wherein $(ZR^7{}_m)_n$ is a divalent group bridging Cp and A; Z being C, Si, Ge, N or P, and the $R^7$ groups, equal to or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups or two $R^7$ can form a aliphatic or aromatic $C_4$–$C_7$ ring;

Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;

A is O, S, $NR^8$, $PR^8$ wherein $R^8$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp;

M is a transition metal belonging to group 4, 5 or to the lanthanide or actinide groups of the Periodic Table of the Elements IUPAC version);

the substituents L, equal to or different from each other, are monoanionic sigma ligands selected from the group consisting of hydrogen, halogen, $R^9$, $OR^9$, $OCOR^9$, $SR^9$, $NR^9{}_2$ and $PR^9{}_2$, wherein $R^9$ is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group, optionally containing one or more Si or Ge atoms; preferably, the substituents L are the same;

m is 1 or 2, and more specifically it is 1 when Z is N or P, and it is 2 when Z is C, Si or Ge;

n is an integer ranging from 0 to 4;

r is 0, 1 or 2; preferably 0 or 1; n is 0 when r is 0;

p is an integer equal to the oxidation state of the metal M minus r+1; i.e. minus 3 when r=2, minus 2 when r=1, and minus 1 when r=0, and ranges from 1 to 4.

In the metallocene compound of formula (XI), the divalent bridge $(ZR^7{}_m)_n$ is preferably selected from the group consisting of $CR^7{}_2$, $(CR^7{}_2)_2$, $(CR^7{}_2)_3$, $SiR^7{}_2$, $GeR^7{}_2$, $NR^7$ and $PR^7$, $R^7$ having the meaning reported above; more preferably, said divalent bridge is $Si(CH_3)_2$, $SiPh_2$, $CH_2$, $(CH_2)_2$, $(CH_2)_3$ or $C(CH_3)_2$.

The variable m is preferably 1 or 2; the variable n ranges preferably from 0 to 4 and, when n>1, the atoms Z can be the same or different from each other, such as in divalent bridges $CH_2$—O, $CH_2$—S and $CH_2$—$Si(CH_3)_2$.

The ligand Cp, which is π-bonded to said metal M, is preferably selected from the group consisting of cyclopentadienyl, mono-, di-, tri- and tetra-methyl cyclopentadienyl; 4-$^t$butyl-cyclopentadienyl; 4-adamantyl-cyclopentadienyl; indenyl; mono-, di-, tri- and tetra-methyl indenyl; 2-methyl indenyl, 3-$^t$butyl-indenyl, 2-methyl-4-phenyl indenyl, 2-methyl-4,5 benzo indenyl; 3-trimethylsilyl-indenyl; 4,5,6,7-tetrahydroindenyl; fluorenyl; 5,10-dihydroindeno[1,2-b]indol-10-yl; N-methyl- or N-phenyl-5,10-dihydroindeno[1,2-b]indol-10-yl; 5,6-dihydroindeno[2,1-b]indol-6-yl; N-methyl-or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl, 2,5-dimethyl-cyclopenta[1,2-b:4,3-b']-dithiophene.

The group A is O, S, $N(^8)$, wherein $R^8$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, preferably $R^8$ is methyl, ethyl, n-propyl, isopropyl, n-butyl, t-butyl, phenyl, p-n-butyl-phenyl, benzyl, cyclohexyl and cyclododecyl; more preferably $R^8$ is t-butyl; or A has the same meaning of Cp.

Non limiting examples of compounds belonging to formula (XI) are the following compounds (when possible in either their meso or racemic isomers, or mixtures thereof):
bis(cyclopentadienyl)zirconium dimethyl;
bis(indenyl)zirconium dimethyl;
bis(tetrahydroindenyl)zirconium dimethyl;
bis(fluorenyl)zirconium dimethyl;
(cyclopentadienyl)(indenyl)zirconium dimethyl;
(cyclopentadienyl)(fluorenyl)zirconium dimethyl;
(cyclopentadienyl)(tetrahydroindenyl)zirconium dimethyl;
(fluorenyl)(indenyl)zirconium dimethyl;
dimethylsilanediylbis(indenyl)zirconium dimethyl,
dimethylsilanediylbis(2-methyl-4-phenylindenyl)zirconium dimethyl,
dimethylsilanediylbis(4-naphthylindenyl)zirconium dimethyl,
dimethylsilanediylbis(2-methylindenyl)zirconium dimethyl,
dimethylsilanediylbis(2-methyl-4-t-butylindenyl)zirconium dimethyl,
dimethylsilanediylbis(2-methyl-4-isopropylindenyl)zirconium dimethyl,
dimethylsilanediylbis(2,4-dimethylindenyl)zirconium dimethyl,
dimethylsilanediylbis(2-methyl-4,5-benzoindenyl)zirconium dimethyl,
dimethylsilanediylbis(2,4,7-trimethylindenyl)zirconium dimethyl,
dimethylsilanediylbis(2,4,6-trimethylindenyl)zirconium dimethyl,
dimethylsilanediylbis(2,5,6-trimethylindenyl)zirconium dimethyl,
methyl(phenyl)silanediylbis(2-methyl-4,6-diisopropylindenyl)-zirconium dimethyl,
methyl(phenyl)silanediylbis(2-methyl-4-isopropylindenyl)-zirconium dimethyl,
1,2-ethylenebis(indenyl)zirconium dimethyl, 1,2-ethylenebis(4,7-dimethylindenyl)zirconium dimethyl,
1,2-ethylenebis(2-methyl-4-phenylindenyl)zirconium dimethyl,
1,4-butanediylbis(2-methyl-4-phenylindenyl)zirconium dimethyl,
1,2-ethylenebis(2-methyl-4,6-diisopropylindenyl)zirconium dimethyl,
1,4-butanediylbis(2-methyl-4-isopropylindenyl)zirconium dimethyl,
1,4-butanediylbis(2-methyl-4,5-benzoindenyl)zirconium dimethyl,
1,2-ethylenebis(2-methyl-4,5-benzoindenyl)zirconium dimethyl,
[4-($\eta^5$-cyclopentadienyl)-4,6,6-trimethyl($\eta^5$-4,5-tetrahydropentalene)]dimethylzirconium,
[4-($\eta^5$-3'-trimethylsilylcyclopentadienyl)-4,6,6-trimethyl ($\eta^5$-4,5-tetrahydropentalene)]dimethylzirconium,
(tert-butylamido)(tetramethyl-$\eta^5$-cyclopentadienyl)-1,2-ethane-dimethyltitanium,
(methylamido)(tetramethyl-$\eta^5$-cyclopentadienyl)dimethylsilyl-dimethyltitanium,
(methylamido)(tetramethyl-$\eta^5$-cyclopentadienyl)-1,2-ethanediyl-dimethyltitanium,
(tertbutylamido)-(2,4-dimethyl-2,4-pentadien-1-yl)dimethylsilyl-dimethyltitanium,
bis(1,3-dimethylcyclopentadienyl)zirconium dimethyl,
methylene(3-methyl-cyclopentadienyl)-7-(2,5-dimethylcyclopentadienyl-[1,2-b:4,3-b']dithiophene)zirconium dimethyl;
methylene(3-isopropyl-cyclopentadienyl)-7-(2,5-dimethyl-cyclopentadienyl-[1,2-b:4,3-b']dithiophene)zirconium dimethyl;
methylene(2,4-dimethyl-cyclopentadienyl)-7-(2,5-dimethylcyclopentadienyl-[1,2-b:4,3-b']dithiophene)zirconium dimethyl;
methylene(2,3,5-trimethyl-cyclopentadienyl)-7-(2,5-dimethylcyclopentadienyl-[1,2-b:4,3-b']dithiophene)zirconium dimethyl;
methylene-1-(indenyl)-7-(2,5-dimethylcyclopentadienyl-[1,2-b:4,3-b']dithiophene)zirconium dimethyl and dimethyl;
methylene-1-(indenyl)-7-(2,5-ditrimethylsilylcyclopentadienyl-[1,2-b:4,3-b']dithiophene)zirconium dimethyl;
methylene-1-(3-isopropyl-indenyl)-7-(2,5-dimethylcyclopentadienyl-[1,2-b:4,3-b']dithiophene)zirconium dimethyl;
methylene-1-(2-methyl-indenyl)-7-(2,5-dimethylcyclopentadienyl-[1,2-b:4,3-b']dithiophene)zirconium dimethyl;
methylene-1-(tetrahydroindenyl)-7-(2,5-dimethylcyclopentadienyl-[1,2-b:4,3-b']dithiophene)zirconium dimethyl;
methylene(2,4-dimethyl-cyclopentadienyl)-7-(2,5-dimethylcyclopentadienyl-[1,2-b:4,3-b']dioxazol)zirconium dimethyl;
methylene(2,3,5-trimethyl-cyclopentadienyl)-7-(2,5-dimethylcyclopentadienyl-[1,2-b:4,3-b']dioxazol)zirconium dimethyl;
methylene-1-(indenyl)-7-(2,5-dimethylcyclopentadienyl-[1,2-b:4,3-b']dioxazol)zirconium dimethyl and dimethyl;
isopropylidene(3-methyl-cyclopentadienyl)-7-(2,5-dimethylcyclopentadienyl-[1,2-b:4,3-b']dithiophene)zirconium dimethyl;
isopropylidene(2,4-dimethyl-cyclopentadienyl)-7-(2,5-dimethylcyclopentadienyl-[1,2-b:4,3-b']dithiophene)zirconium dimethyl;
isopropylidene(2,4-diethyl-cyclopentadienyl)-7-(2,5-dimethylcyclopentadienyl-[1,2-b:4,3-b']dithiophene)zirconium dimethyl;
isopropylidene(2,3,5-trimethyl-cyclopentadienyl)-7-(2,5-dimethylcyclopentadienyl-[1,2-b:4,3-b']dithiophene)zirconium dimethyl;
isopropylidene-1-(indenyl)-7-(2,5-dimethylcyclopentadienyl-[1,2-b:4,3-b']dithiophene)zirconium dimethyl;
isopropylidene-1-(2-methyl-indenyl)-7-(2,5-dimethylcyclopentadienyl-[1,2-b:4,3-b']dithiophene)zirconium dimethyl;
dimethylsilandiyl-1-(2-methyl-indenyl)-7-(2,5-dimethylcyclopentadienyl-[1,2-b:4,3-b']dithiophene)hafnium dimethyl;
dimethylsilanediyl(3-tert-butyl-cyclopentadienyl)(9-fluorenyl)zirconium dimethyl,
dimethylsilanediyl(3-isopropyl-cyclopentadienyl)(9-fluorenyl)zirconium dimethyl,
dimethylsilanediyl(3-methyl-cyclopentadienyl)(9-fluorenyl)zirconium dimethyl,
dimethylsilanediyl(3-ethyl-cyclopentadienyl)(9-fluorenyl) zirconium dimethyl,
1-2-ethane(3-tert-butyl-cyclopentadienyl)(9-fluorenyl)zirconium dimethyl,
1-2-ethane(3-isopropyl-cyclopentadienyl)(9-fluorenyl)zirconium dimethyl,
1-2-ethane(3-methyl-cyclopentadienyl)(9-fluorenyl)zirconium dimethyl,
1-2-ethane(3-ethyl-cyclopentadienyl)(9-fluorenyl)zirconium dimethyl,
dimethylsilandiylbis-6-(3-methylcyclopentadienyl-[1,2-b]-thiophene)dimethyl;
dimethylsilandiylbis-6-(4-methylcyclopentadienyl-[1,2-b]-thiophene)zirconium dimethyl;
dimethylsilandiylbis-6-(4-isopropylcyclopentadienyl-[1,2-b]-thiophene)zirconium dimethyl;
dimethylsilandiylbis-6-(4-ter-butylcyclopentadienyl-[1,2-b]-thiophene)zirconium dimethyl;
dimethylsilandiylbis-6-(3-isopropylcyclopentadienyl-[1,2-b]-thiophene)zirconium dimethyl;
dimethylsilandiylbis-6-(3-phenylcyclopentadienyl-[1,2-b]-thiophene)zirconium dimethyl;
dimethylsilandiylbis-6-(2,5-dimethyl-3-phenylcyclopentadienyl-[1,2-b]-thiophene)zirconium dimethyl;
dimethylsilandiylbis-6-[2,5-dimethyl-3-(2-methylphenyl)cyclopentadienyl-[1,2-b]-thiophene]zirconium dimethyl;
dimethylsilandiylbis-6-[2,5-dimethyl-3-(2,4,6-trimethylphenyl)cyclopentadienyl-[1,2-b]-thiophene]zirconium dimethyl;
dimethylsilandiylbis-6-[2,5-dimethyl-3-mesitylenecyclopentadienyl-[1,2-b]-thiophene]zirconium dimethyl;
dimethylsilandiylbis-6-(2,4,5-trimethyl-3-phenylcyclopentadienyl-[1,2-b]-thiophene)zirconium dimethyl;
dimethylsilandiylbis-6-(2,5-diethyl-3-phenylcyclopentadienyl-[1,2-b]-thiophene)zirconium dimethyl;
dimethylsilandiylbis-6-(2,5-diisopropyl-3-phenylcyclopentadienyl-[1,2-b]-thiophene)zirconium dimethyl;
dimethylsilandiylbis-6-(2,5-diter-butyl-3-phenylcyclopentadienyl-[1,2-b]-thiophene)zirconium dimethyl;
dimethylsilandiylbis-6-(2,5-ditrimethylsilyl-3-phenylcyclopentadienyl-[1,2-b]-thiophene)zirconium dimethyl;
dimethylsilandiylbis-6-(3-methylcyclopentadienyl-[1,2-b]-silole)zirconium dimethyl;
dimethylsilandiylbis-6-(3-isopropylcyclopentadienyl-[1,2-b]-silole)zirconium dimethyl;
dimethylsilandiylbis-6-(3-phenylcyclopentadienyl-[1,2-b]-silole)zirconium dimethyl;
dimethylsilandiylbis-6-(2,5-dimethyl-3-phenylcyclopentadienyl-[1,2-b]-silole)zirconium dimethyl;

dimethylsilandiylbis-6-[2,5-dimethyl-3-(2-methylphenyl)
cyclopentadienyl-[1,2-b]-silole]zirconium dimethyl;
dimethylsilandiylbis-6-[2,5-dimethyl-3-(2,4,6-trimeth-
ylphenyl)cyclopentadienyl-[1,2-b]-silole]zirconium dim-
ethyl;
dimethylsilandiylbis-6-[2,5-dimethyl-3-mesitylenecyclo-
pentadienyl-[1,2-b]-silole]zirconium dimethyl;
dimethylsilandiylbis-6-(2,4,5-trimethyl-3-phenylcyclopen-
tadienyl-[1,2-b]-silole)zirconium dimethyl;
[dimethylsilyl(tert-butylamido)][(N-methyl-1,2-dihydrocy-
clopenta[2,1-b]indol-2-yl)]titanium dimethyl;
[dimethylsilyl(tert-butylamido)][(6-methyl-N-methyl-1,2-
dihydrocyclopenta[2,1-b]indol-2-yl)]titanium dimethyl;
[dimethylsilyl(tert-butylamido)][(6-methoxy-N-methyl-1,2-
dihydrocyclopenta[2,1-b]indol-2-yl)]titanium dimethyl;
[dimethylsilyl(tert-butylamido)][(N-ethyl-1,2-dihydrocy-
clopenta[2,1-b]indol-2-yl)]titanium dimethyl;
[dimethylsilyl(tert-butylamido)][(N-phenyl-1,2-dihydrocy-
clopenta[2,1-b]indol-2-yl)]titanium dimethyl;
[dimethylsilyl(tert-butylamido)][(6-methyl-N-phenyl-1,2di-
hydrocyclopenta[2,1-b]indol2-yl)]titanium dimethyl;
[dimethylsilyl(tert-butylamido)][(6-methoxy-N-phenyl-1,2-
dihydrocyclopenta[2,1-b]indol2-yl)]titanium dimethyl;
[dimethylsilyl(tert-butylamido)][(N-methyl-3,4-dimethyl-1,
2-dihydrocyclopenta[2,1-b]indol-2-yl)]titanium dim-
ethyl;
[dimethylsilyl(tert-butylamido)][(N-ethyl-3,4-dimethyl-1,2-
dihydrocyclopenta[2,1-b]indol-2-yl)]titanium dimethyl;
[dimethylsilyl(tert-butylamido)][(N-phenyl-3,4-dimethyl-1,
2-dihydroclopenta[2,1-b]indol-2-yl)]titanium dimethyl;
as well as the corresponding dichloro, hydrochloro and
dihydro compounds and the corresponding $\eta^4$-butadiene
compounds.

When A is $N(R^8)$, a suitable class of metallocene complexes (A) for use in the catalysts complexes of the invention comprises the well-known constrained geometry catalysts, as described in EP-A-0 416 815, EP-A-0 420 436, EP-A-0 671 404, EP-A-0 643 066 and WO-A-91/04257.

A further preferred class of transition metal organometallic catalyst compounds is a late transition metal complex of formula (XII) or (XIII):

(XII)

(XIII)

wherein $M^a$ is a metal belonging to Group 8, 9, 10 or 11 of the Periodic Table of the Elements (new IUPAC notation); $L^a$ is a bidentate or tridentate ligand of formula (XIV):

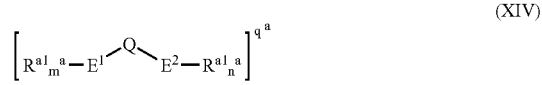
(XIV)

wherein:
Q is a $C_1-C_{50}$ bridging group linking $E^1$ and $E^2$, optionally containing one or more atoms belonging to Groups 13–17 of the Periodic Table;
$E^1$ and $E^2$, the same or different from each other, are elements belonging to Group 15 or 16 of the Periodic Table and are bonded to said metal $M^a$;
the substituents $R^{a1}$, equal to or different from each other, are selected from the group consisting of hydrogen, linear or branched, saturated or unsaturated $C_1-C_{20}$ alkyl, $C_3-C_{20}$ cycloalkyl, $C_6-C_{20}$ aryl, $C_7-C_{20}$ alkylaryl and $C_7-C_{20}$ arylalkyl radicals, optionally containing one or more atoms belonging to groups 13–17 of the Periodic Table of the Elements (such as B, Al, Si, Ge, N, P, O, S, F and Cl atoms); or two $R^{a1}$ substituents attached to the same atom $E^1$ or $E^2$ form a saturated, unsaturated or aromatic $C_4-C_7$ ring, having from 4 to 20 carbon atoms;
$m^a$ and $n^a$ are independently 0, 1 or 2, depending on the valence of $E^1$ and $E^2$, so to satisfy the valence number of $E^1$ and $E^2$; $q^a$ is the charge of the bidentate or tridentate ligand so that the oxidation state of $M^aX^a_pX^{a'}_s$ or $M^aA^a$ is satisfied, and the compound (XII) or (XIII) is overall neutral;
$X^a$, the same or different from each other, are monoanionic sigma ligands selected from the group consisting of hydrogen, halogen, $R^a$, $OR^a$, $OSO_2CF_3$, $OCOR^a$, $SR^a$, $-NR_2$ and $PR^a_2$ groups, wherein the $R^a$ substituents are linear or branched, saturated or unsaturated, $C_1-C_{20}$ alkyl, $C_3-C_{20}$ cycloalkyl, $C_6-C_{20}$ aryl, $C_7-C_{20}$ alkylaryl or $C_7-C_{20}$ arylalkyl radicals, optionally containing one or more atoms belonging to groups 13–17 of the Periodic Table of the Elements (new IUPAC notation), such as B, N, P, Al, Si, Ge, O, S and F atoms; or two $X^a$ groups form a metallacycle ring containing from 3 to 20 carbon atoms; the substituents $X^a$ are preferably the same;
$p^a$ is an integer ranging from 0 to 3, so that the final compound (XII) or (XIII) is overall neutral; and
$A^a$ is a $\pi$-allyl or a $\pi$-benzyl group.

Non limiting examples of late transition metal complexes are those described in WO 96/23010, WO 97/02298, WO 98/40374 and J. Am. Chem. Soc. 120:4049–4050, 1998. Brookhart et al, J. Am. Chem. Soc. 1995, 117, 6414 and Brookhart et al, J. Am. Chem. Soc., 1996, 118, 267, Brookhart et al, J. Am. Chem. Soc. 1998, 120, 4049, Gibson et al, Chem. Commun. 1998, 849, WO 96/27439 and Chem. Ber./Recl. (1997), 130(3), 399–403. The organometallic compounds and the salts according to the invention exert good activities as cocatalysts in olefin polymerization process; moreover, they are easy to prepare and do not lead to the release of undesired by-products after the metallocene activation. Further they are stable and produce stable catalyst compositions under polymerization conditions.

The molar ratio between the component (B) and the transition metal organometallic compound (A), calculated as the molar ratio between the metal Mt of the Lewis acid and the metal of the transition metal organometallic catalyst compound, preferably ranges from 10:1 to 1:10, more preferably from 2:1 to 1:2, and even more preferably is about 1:1.

According to the invention, component (B) of the catalyst system can suitably comprise a mixture of two or more organometallic compounds or salts of the invention. Moreover, component (B) can be used in combination with other compatible cocatalysts known in the state of the art, such as alumoxane compounds.

The catalyst system of the invention may also comprise one or more aluminum compounds of formula $AlR^{10}_{3-z}W_z$, acting as scavenger, wherein $R^{10}$ can be $C_1-C_{10}$ alkyl, alkenyl or alkylaryl radicals, optionally containing one or more Si or Ge atoms, z is 0, 1 or 2 or a non integer number ranging from 0 to 2; W is hydrogen, chlorine, bromine or iodine; non-limiting examples of aluminum compounds are trimethylaluminum (TMA), tris(2,4,4-trimethyl-pentyl)aluminum (TIOA), tris(2-methyl-propyl)aluminum (TIBA), tris(2,3,3-trimethyl-butyl)aluminum, tris(2,3-dimethyl-hexyl)aluminum, tris(2,3-dimethyl-butyl)aluminum, tris(2, 3-dimethyl-pentyl)aluminum, tris(2,3-dimethyl-heptyl)aluminum, tris(2-methyl-3-ethyl-pentyl)aluminum and tris(2-ethyl-3,3-dimethyl-butyl).

Another example of compound that can act as scavenger are alumoxane compounds containing at least one group of the type:

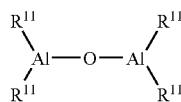

wherein the $R^{11}$ substituents, which may be the same or different, are described above.

In particular, alumoxanes of the formula:

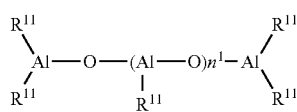

can be used in the case of linear compounds, wherein $n^1$ is 0 or an integer from 1 to 40 and the $R^{11}$ substituents are defined as above, or alumoxanes of the formula:

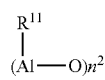

can be used in the case of cyclic compounds, wherein $n^2$ is an integer from 2 to 40 and the $R^{11}$ substituents are defined as above.

Examples of alumoxanes suitable as scavenger according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting alumoxanes are those disclosed in WO 99/21899.

The catalyst system of the invention may be formed prior to its introduction into a polymerization reactor or in situ in the reactor, by contacting the above-described components (A), (B) and optionally an alkylating agent.

According to an embodiment of the invention, components (A), (B) and optionally an alkylating agent are first contacted and then introduced into the reactor, wherein separately an aluminum compound $AlR^{10}_{3-z}W_z$, or an alumoxane has been introduced. Alternatively, components (A), (B) and optionally an alkylating agent and said aluminum compound $AlR^{10}_{3-z}W_z$ or said alumoxane may be contacted together prior to their introduction into the reactor.

The catalysts system of the present invention can be used on inert supports. This may be achieved by depositing said transition metal organometallic catalyst compound (A), or the product of the reaction thereof with the component (B), or the component (B) and subsequently said transition metal organometallic compound before or after the optional treatment with said alkylating agent, on inert supports such as silica, alumina, styrene/divinylbenzene copolymers, polyethylene or polypropylene.

The thus obtained solid compound can be suitably used in gas phase polymerization.

The catalysts of the present invention can be used in the polymerization reactions of olefins.

Therefore, according to a further object, the invention provides a process for the polymerization of one or more olefins comprising contacting one or more olefins under polymerization conditions in the presence of a catalyst system as described above.

Olefins which can be polymerized with the process of the present invention are, for instance, α-olefins of formula $CH_2$=CHR, wherein R is hydrogen or a $C_1$–$C_{20}$ alkyl radical.

The catalysts according to the present invention can be conveniently used in the homopolymerization of ethylene, in particular for the preparation of HDPE, and in the copolymerization of ethylene, in particular for the preparation of LLDPE. Suitable comonomers in ethylene copolymers are α-olefins of formula $CH_2$=CHR', wherein R' is a linear, branched or cyclic $C_1$–$C_{20}$ alkyl radical or cycloolefins. Examples of such olefins are propylene, 1-butene, 1-pentene, 4-methyl-1-pentene, 1-hexene, 1-octene, allyl-cyclohexane, cyclopentene, cyclohexene, norbornene and 4,6-dimethyl-1-heptene.

Further suitable comonomers in said ethylene copolymers are polyenes, in particular conjugated or non-conjugated, linear or cyclic dienes, such as 1,4hexadiene, isoprene, 1,3-butadiene, 1,5-hexadiene and 1,6-heptadiene.

The catalysts of the invention can be suitably used in propylene homopolymerization, or copolymerization in particular for the production of isotactic polypropylene.

Moreover, the catalysts of the invention can be suitably used in the preparation of elastomeric copolymers of ethylene with α-olefins of formula $CH_2$=CHR", wherein R" is a $C_1$–$C_{10}$ alkyl radical, such as propylene, 1-butene, 4-methyl-1-pentene, 1-hexene and 1-octene; said copolymers may optionally contain minor proportions of units deriving from polyenes.

According to a further embodiment, the catalysts according to the present invention are used in the preparation of cycloolefin polymers. Monocyclic and polycyclic olefin monomers can be either homopolymerized or copolymerized, also with linear olefin monomers.

The polymerization processes of the present invention can be carried out in liquid phase, optionally in the presence of an inert hydrocarbon solvent, or in gas phase. Said hydrocarbon solvent can be either aromatic (such as toluene) or aliphatic (such as propane, hexane, heptane, isobutane, cyclohexane and 2,2,4-trimethylpentane).

The polymerization temperature preferably ranges from 0° C. to 250° C.; in the preparation of HDPE and LLDPE, it is preferably comprised between 20° C. and 150° C. and, more particularly between 40° C. and 90° C.; in the preparation of elastomeric copolymers, it is preferably comprised between 0° C. and 200° C., and more preferably between 20° C. and 100° C. The molecular weight of the polymers can be varied simply by varying the polymerization temperature, the type or the concentration of the catalyst components, or by using molecular weight regulators, such as hydrogen.

The molecular weight distribution can be varied by using mixtures of different metallocene complexes or by carrying out the polymerization in several stages which differ in the polymerization temperature and/or the concentrations of molecular weight regulator.

The polymerization yield depends on the purity of the transition metal organometallic catalyst compound (A) in the catalyst, therefore, said compound can be used as such or can be subjected to purification treatments before use.

The following examples are given for illustrative and not limiting purposes.

GENERAL PROCEDURES AND CHARACTERIZATIONS

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. Indole (Aldrich, purity 98% or Fluka, purity 99%), N-methylindole (Aldrich, purity 97%), N-methylpyrrole (Aldrich, purity 99%), $NEt_3$ (Aldrich, 99.5%) and $B(C_6F_5)_3$ (Boulder Scientific Company) were used as received.

$^1$H-NMR and $^{13}$C-NMR

The proton and carbon spectra of the compounds were obtained using a Bruker DPX 200 spectrometer operating in the Fourier transform mode at room temperature at 200.13 MHz and 50.33 MHz respectively. The samples were dissolved in $CD_2Cl_2$ or $C_6D_6$. As reference the residual peak of $CHDCl_2$ or $C_6HD_5$ in the $^1$H spectra (5.35 ppm and 7.15 ppm, respectively) and the peak of the solvent in the $^{13}$C spectra (53.80 ppm for $CD_2Cl_2$ and 128.00 ppm for $C_6D_6$) were used. Proton spectra were acquired with a 15° pulse and 2 seconds of delay between pulses; 32 transients were stored for each spectrum. The carbon spectra were acquired with a 45° pulse and 6 seconds of delay between pulses; about 512 transients were stored for each spectrum. $CD_2Cl_2$ (Aldrich, 99.8% atom D) was used as received, while $C_6D_6$ (Aldrich, 99% atom D) was dried over activated 4 A° molecular sieves before use. Preparation of the samples was carried out under nitrogen using standard inert atmosphere techniques.

SYNTHESIS OF THE ORGANOMETALLIC BORON COMPOUNDS

EXAMPLE 1

Synthesis of 2-[tris(pentafluorophenyl)borane]-3H-1-methylindole [A-1]

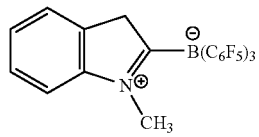

A yellow solution of 1-methylindole (97%, 0.78 g, MW=131.18, 5.8 mmol) in 10 ml of dichloromethane was added at room temperature to a white suspension of $B(C_6F_5)_3$ (99.4%, 2.97 g, MW=511.99, 5.8 mmol) in 10 ml of dichloromethane in a 25 mL Schlenk flask. The resulting orange solution was stirred at room temperature for ten days and analyzed by $^1$H NMR at different times. During this time the color of the solution turned from orange to dark bordeaux; NMR analyses showed a slow conversion of the starting 1-methylindole to the product. The solvent was evaporated in vacuum and the obtained solid was suspended in a 9/1 pentane/dicloromethane mixture and filtered. The residue on the frit was a fuchsia solid (3.27 g, yield 87.8%).

The product was completely characterized by $^1$H NMR, $^{13}$C NMR, DEPT (Distorsionless Enhancement by Polarization Transfer), NOESY (Nuclear Overhauser Enhancement Spectroscopy), COSY (Correlation Spectroscopy), HSQC (Heteronuclear Single Quantum Coherence) and HMBC (Heteronuclear Multiple Bond Correlation) analyses.

$^1$H NMR ($CD_2Cl_2$, δ, ppm): 3.77 (s, 3H, N—$CH_3$); 4.59 (broad AB system, 2H3,H3'); 7.47–7.69 (m, 4H, Ar).

$^1$H NMR ($C_6D_6$, δ, ppm): 2.84 (s, 3H, N—$CH_3$); 4.04 (broad AB system, 2H, H3,H3'); 6.42–6.51 (m, 1H, H7); 6.83–6.98 (m, 3H, Ar).

$^{13}$C NMR ($CD_2Cl_2$, δ, ppm): 36.55 ($CH_3$); 48.33 (C3); 113.59 (C7); 125.22 (C4); 128.97 (C5 or C6); 129.22 (C6 or C5); 134.18 (C3a); 147.06 (C7a); 214.34–217.43 (m, C2).

melting point 126.7° C.–127.8° C.

EXAMPLE 2

Synthesis of tris(pentafluorophenyl)-(1-methylindol-2-yl)-borate(1-)triethylammonium [A-2]

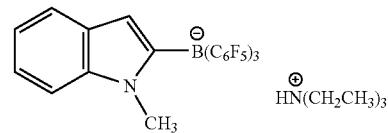

A colorless solution of triethylamine (99.5%, 0.167 g, MW=101.19, 1.6 mmol) (dichloromethane, 6 mL) was added at room temperature to a bordeaux solution of 2-[tris(pentafluorophenyl)borane]-3H-1-methylindole (1.048 g, MW=643.16, 1.6 mmol) (dichloromethane, 4 mL) in a 10 mL Schlenk flask. The resulting solution was stirred at room temperature for an hour and its color turned from the initially orange to yellow. Then the solvent was removed in vacuum to give a yellow solid as product, 1.11 g, yield 93.2%).

$^1$H NMR ($CD_2Cl_2$, δ, ppm): 1.03 (t, 9H, J=7.24 Hz, N($CH_2CH_3$)$_3$); 2.60 (q, 6H, J=7.24 Hz, N($CH_2CH_3$)$_3$); 3.40 (bs, 1H, NH); 3.51 (s, 3H, N—$CH_3$); 6.19 (s, 1H, H3); 6.95–7.13 (m, 2H, H5,H6); 7.23–7.29 (m, 1H, H7); 7.41–7.48 (m, 1H, H4).

$^{13}$C NMR ($CD_2Cl_2$, δ, ppm): 8.56 (N($CH_2CH_3$)$_3$); 31.84 (N—$CH_3$); 47.32 (N($CH_2CH_3$)$_3$); 104.75 (C3); 109.35 (C7); 118.29 and 118.35 (C4 and C5 or C6); 119.19 (C6 or C5); 128.79 (C3a); 139.47 (C7a).

EXAMPLE 3

Synthesis of 2-[tris(pentafluorophenyl)borane]-5H-1-methylpyrrole [A-3]

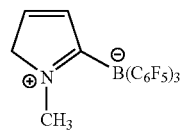

A light yellow solution of 1-methylpyrrole (99%, 0.503 g, MW=81.12, 6.1 mmol) (dichloromethane, 10 mL) was added at room temperature to a white-gray suspension of $B(C_6F_5)_3$ (99.4%, 3.18 g, MW=511.99, 6.2 mmol) (dichloromethane, 10 mL). The resulting orange cloudy solution was stirred at room temperature for three days and then the solvent was removed under reduced pressure. The obtained orange powder was suspended with a ½ dichloromethane/pentane mixture and filtered. The filtrate was a dark pink solid (the desired product together with unidentified species), whereas the residue on the frit was a very light yellow powder (2.42 g of the desired product, yield 66.5%).

$^1$H NMR (CD$_2$Cl$_2$, δ, ppm): 3.55 (s, 3H, CH$_3$); 4.70 (bs, 2H, H5, H5'); 6.91 (bs, 1H, H3); 7.42 (d, J=5.87 Hz, 1H, H4).

$^{13}$C NMR (CD$_2$Cl$_2$, δ, ppm): 38.12 (CH$_3$); 69.81 (C5); 108.42 (C2); 137.33 (C3); 146.06 (C4). Melting point 116.6° C.–118.2° C.

EXAMPLE 4

Synthesis of tris(pentafluorophenyl)-(1-methypyrrol-2-yl)-borate(1-) triethylammonium [A-4]

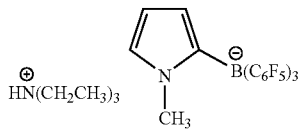

A colorless solution of triethylamine (99.5%, 0.167 g, MW=101.19, 1.6 mmol) (dichloromethane, 6 mL) was added at room temperature to an orange solution of 2-[tris(pentafluorophenyl)borane]-5H-1-methylpyrrole [A-3] (1.048 g, MW=643.16, 1.6 mmol) (dichloromethane, 6 mL) in a 25 mL Schlenk flask. The resulting light yellow solution was stirred at room temperature for an hour. Then the solvent was removed under reduced pressure to give a white-gray solid as product (0.892 g, yield 97.9%).

$^1$H NMR (CD$_2$Cl$_2$, δ, ppm): 1.22 (t, 9H, J=7.34 Hz, N(CH$_2$CH$_3$)$_3$); 3.03 (q, 6H, J=7.34 Hz, N(CH$_2$CH$_3$)$_3$); 3.32 (s, 3H, N—CH$_3$); 5.76 (bd, 1H, J=2.64 Hz, H3); 5.96 (d, 1H, J=3.23 Hz, H4); 6.10 (bs, 1H, NH); 6.64 (bs, 1H, H5).

$^{13}$C NMR (CD$_2$Cl$_2$, δ, ppm): 8.82 (N(CH$_2$CH$_3$)$_3$); 35.94 (N—CH$_3$); 47.32 (N(CH$_2$CH$_3$)$_3$); 104.40 (C4); 111.85 (C3); 122.95 (C5), 146.20 (C2).

Synthesis of bis(indenyl)zirconium dimethyl 29.6 mL of a solution of MeLi 1.6 M in Et$_2$O (47.4 mmol) were added at room temperature to a solution of 3 g of indene (23.7 mmol, Aldrich, 91.8 %) in 30 mL of Et$_2$O, over a period of about 5 minutes (exothermic reaction). The mixture was stirred for 30 minutes to give an orange solution.

2.76 g of ZrCl$_4$ (11.84 mmol) were slurried in 30 mL of pentane. The ZrCl$_4$ slurry in pentane was quickly added to the Li salt solution in Et$_2$O (exothermic reaction). The resulting reaction mixture was stirred for 2 hours and then brought to dryness under reduced pressure. The light brown solid obtained was extracted with 100 mL of pentane (Soxhlet, 4.5 hours) and then the filtrate was evaporated to dryness under reduced pressure to give 3.2 g (77% yield) of a light yellow solid, which was characterized by $^1$H NMR as pure Ind$_2$ZrMe$_2$.

$^1$H-NMR (C$_6$D$_6$, δ, ppm): –0.78 (s, 6H, Zr—CH$_3$), 5.62 (t, 2H, Cp-H(2)), 5.80 (d, 4H, Cp-H(1,3)); 6.87–6.92 (m, 4H, Ar), 7.19–7.23 (m, 4H, Ar).

Preparation of the Catalyst System 0.1 μmol of bis(indenyl)zirconium dimethyl prepared as reported above, was dissolved in 2 mL of toluene in a 10 mL Schlenk under nitrogen atmosphere and then the cocatalyst indicated in table 1 in 2 mL toluene was quickly added (Zr/cocat molar ration 1:1.1).

Polymerization Examples 5–8

Ethylene Polymerization

Ethylene polymerizations were carried out in a 260-mL Büchi glass autoclave equipped with magnetic stirrer, thermocouple and feeding line for the monomer, purified with nitrogen and kept in a thermostatic bath. Under ethylene purge, heptane (100 mL) and Al(i-Bu)$_3$ (0.1 mmol) were introduced, the temperature was brought to 80° C. and the reactor vented to remove residual nitrogen, then pressurized with ethylene up to 0.5 bar-g. The catalytic system, prepared as described above, was siphoned into the reactor by means of a Teflon cannula, and the ethylene partial pressure was raised to 4 bar-g. The polymerization was carried out at 80° C. for 15 minutes, by maintaining a constant ethylene partial pressure, then stopped by degassing the reactor and by adding 2 mL of methanol. The polymer was precipitated with 200 mL of acetone, filtered, washed with acetone and dried overnight at 60° C. reduced pressure. The polymerization results are reported in table 1.

TABLE 1

| Example | Cocatalyst | yield (g) | kg$_{PE}$/(mmol$_{Zr}$ × h) |
|---|---|---|---|
| 5 | A-1 | 1.90 | 7.6 |
| 6 | A-2 | 1.81 | 7.2 |
| 7 | A-3 | 2.15 | 8.6 |
| 8 | A-4 | 6.87 | 27.5 |

The invention claimed is:
1. An organometallic compound obtained by contacting:
a) a compound having the following formula (I):

wherein
R$^a$ is a linear or branched, saturated or unsaturated, C$_1$–C$_{10}$ alkyl, C$_6$–C$_{20}$ aryl, C$_7$–C$_{20}$ arylalkyl or C$_7$–C$_{20}$ alkylaryl group, optionally containing O, S, N, P, Si or halogen atoms; or R$^a$ can join R$^d$ to form a C$_4$–C$_7$ ring;
R$^b$, R$^c$ and R$^d$, equal to or different from each other, are hydrogen atoms, halogen atoms, linear or branched, saturated or unsaturated, C$_1$–C$_{10}$ alkyl, C$_6$–C$_{20}$ aryl, C$_7$–C$_{20}$ arylalkyl or C$_7$–C$_{20}$ alkylaryl groups, optionally containing O, S, N, P, Si or halogen atoms, or two or more adjacent substituents R$^b$, R$^c$, and R$^d$ form one or more C$_4$–C$_7$ rings, optionally containing O, S, N, P or Si atoms, that can bear substituents; with
b) a Lewis acid of formula (II):

MtR$^1$$_3$ (II)

wherein Mt is a metal belonging to Group 13 of the Periodic Table of the Elements; $R^1$, equal to or different from each other, are halogen atoms, halogenated $C_6$–$C_{20}$ aryl or halogenated $C_7$–$C_{20}$ alkylaryl groups; two $R^1$ groups can also form with the metal Mt one condensed ring.

2. The organometallic compound according to claim 1 wherein Mt is B or Al; and the substituents $R^1$ are $C_6F_5$, $C_6F_4H$, $C_6F_3H_2$, $C_6H_3(CF_3)_2$, perfluoro-biphenyl, heptafluoro-naphthyl, hexafluoro-naphthyl or pentafluoro-naphthyl.

3. The organometallic compound according to claim 1 having formula (III):

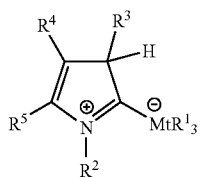

(III)

wherein
Mt is a metal belonging to Group 13 of the Periodic Table of the Elements (IUPAC); $R^1$, equal to or different from each other, are halogen atoms, halogenated $C_6$–$C_{20}$ aryl or halogenated $C_7$–$C_{20}$ alkylaryl groups; or two $R^1$ groups can form with the metal Mt one condensed ring; the substituents $R^5$, $R^4$ and $R^3$ equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^3$, $R^4$ and $R^5$ form one or more $C_4$–$C_7$ rings, optionally containing O, S, N, P or Si;

$R^2$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms or $R^2$ can join $R^5$ to form a $C_4$–$C_7$ ring.

4. The organometallic compound according to claim 3 wherein Mt is B or Al; the substituents $R^1$, equal to or different from each other, are $C_6F_5$, $C_6F_4H$, $C_6F_3H_2$, $C_6H_3(CF_3)_2$, perfluoro-biphenyl, heptafluoro-naphthyl, hexafluoro-naphthyl or pentafluoro-naphthyl; $R^4$ and $R^5$ form one $C_5$–$C_6$ aromatic ring, optionally containing O, S, N, or P atoms, that can bear substituents; $R^2$ is a $C_1$–$C_{10}$ alkyl or $C_6$–$C_{20}$ aryl group; and $R^3$ is hydrogen.

5. The organometallic compound according to claim 3 having formula (V):

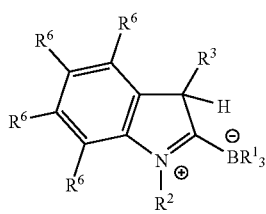

(V)

wherein
B is a boron atom;

the substituents $R^6$, the same or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups optionally containing O, S, N, P, Si or halogen atoms, or two or more adjacent substituents $R^6$ form one or more $C_4$–$C_7$, optionally containing O, S, N, P or Si atoms rings that can bear substituents.

6. The organometallic compound according to claim 1 having formula (IV):

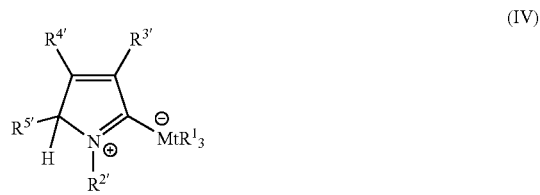

(IV)

wherein
the substituents $R^{3'}$, $R^{4'}$ and $R^{5'}$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^{3'}$, $R^{4'}$ and $R^{5'}$ form one or more $C_4$–$C_7$ rings, optionally containing O, S, N, P or Si atoms, that can bear substituents; said rings can be aliphatic and optionally contain double bonds; with the proviso that said rings are not aromatic;

$R^{2'}$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^{2'}$ can join $R^{5'}$ to form a $C_4$–$C_7$ ring.

7. The organometallic compound according to claim 6 wherein $R^{2'}$ is a $C_1$–$C_{10}$ alkyl, or $C_6$–$C_{20}$ aryl group; the substituents $R^{3'}$, $R^{4'}$ and $R^{5'}$, equal to or different from each other, are hydrogen atoms, linear or branched, saturated or unsaturated, $C_1$–$C_{10}$ alkyl, optionally containing O, S, N, P, Si or halogen atoms, or two or more adjacent substituents $R^{3'}$, $R^{4'}$ and $R^{5'}$ form one or more $C_4$–$C_7$ rings optionally containing O, S, N, P or Si atoms, that can bear substituents; said rings can be aliphatic and optionally contain double bonds, with the proviso that said rings are not aromatic.

8. The organometallic compound according to claim 6 having formula (VI):

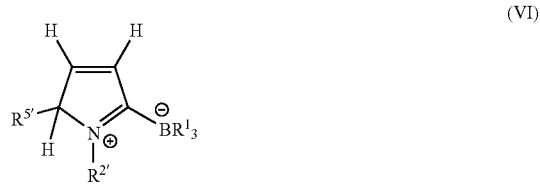

(VI)

wherein
the substituent $R^{5'}$ is a $C_1$–$C_{20}$ alkyl group.

9. A salt obtained by contacting, in any order:
a) a compound having formula (I):

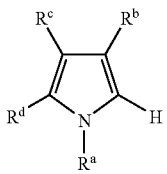
(I)

wherein
$R^a$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^a$ can join $R^d$ to form a $C_4$–$C_7$ ring;
$R^b$, $R^c$ and $R^d$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{10}$ alkylaryl groups, optionally containing O, S, N, P, Si or halogen atoms, or two or more adjacent substituents $R^b$, $R^c$, and $R^d$ form one or more $C_4$–$C_7$ rings, optionally containing O, S, N, P or Si atoms, that can bear substituents;
b) a Lewis acid of formula (II):

$MtR^1_3$ (II)

wherein Mt is a metal belonging to Group 13 of the Periodic Table of the Elements; $R^1$, equal to or different from each other, are halogen atoms, halogenated $C_6$–$C_{20}$ aryl or halogenated $C_7$–$C_{20}$ alkylaryl groups; two $R^1$ groups can also form with the metal Mt one condensed ring; and
c) a compound of formula $KR^f_3$ wherein K is a nitrogen (N) or phosphorous (P) atom; $R^f$, equal to or different from each other, are linear or branched, saturated or unsaturated, $C_1$–$C_{30}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two $R^f$ can form one $C_4$–$C_7$ ring, optionally containing O, S, N, P or Si atoms, that can bear substituents.

10. The salt according to claim 9 wherein K is nitrogen; and $R^f$ is selected from the group consisting of linear or branched, saturated or unsaturated, $C_1$–$C_{30}$ alkyl.

11. The salt according to claim 9 having formula (VII):

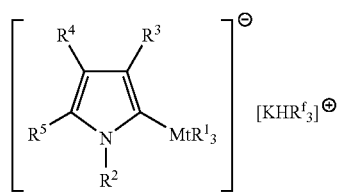
(VII)

wherein $R^1$, equal to or different from each other, are halogen atoms, halogenated $C_6$–$C_{20}$ aryl or halogenated $C_7$–$C_{20}$ alkylaryl groups; or two $R^1$ groups can form with the metal Mt one condensed ring; the substituents $R^5$, $R^4$ and $R^3$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^3$, $R^4$ and $R^5$ form one or more $C_4$–$C_7$ rings, optionally containing O, S, N, P or Si;
$R^2$ is a linear or branched, saturated or unsaturated, $C_1$–$C_{10}$ alkyl, $C_6$–$C_{20}$ aryl, $C_7$–$C_{20}$ arylalkyl or $C_7$–$C_{10}$ alkylaryl group, optionally containing O, S, N, P, Si or halogen atoms or $R^2$ can join $R^5$ to form a $C_4$–$C_7$ ring.

12. The salt according to claim 11 having formula (IX):

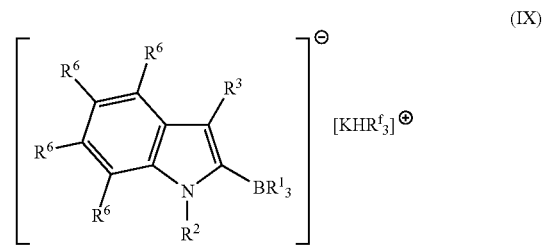
(IX)

wherein B is a boron atom.

13. The salt according to claim 9 having formula (VIII):

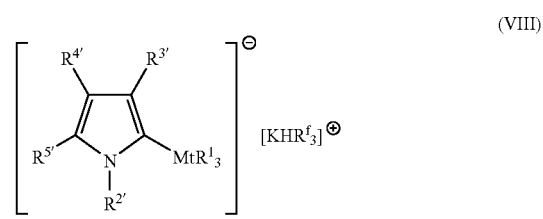
(VIII)

wherein $R^1$, equal to or different from each other, are halogen atoms, halogenated $C_6$–$C_{20}$ aryl or halogenated $C_7$–$C_{10}$ alkylaryl groups; two $R^1$ groups can also form with the metal Mt one condensed ring; the substituents $R^{3'}$, $R^{4'}$ and $R^{5'}$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^{3'}$, $R^{4'}$ and $R^{5'}$ form one or more $C_4$–$C_7$ rings, optionally containing O, S, N, P or Si atoms, that can bear substituents; said rings can be aliphatic and optionally contain double bonds; with the proviso that said rings are not aromatic;
$R^{2'}$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^{2'}$ can join $R^{5'}$ to form a $C_4$–$C_7$ ring.

14. The salt according to claim 13 having formula (X):

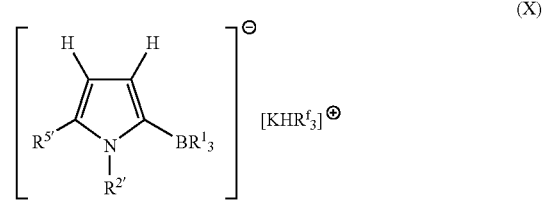
(X)

wherein B is a boron atom.

15. A catalyst system for the polymerization of olefins comprising the product obtained by contacting:
(A) at least one transition metal organometallic compound, and
(B) an organometallic compound obtained by contacting:
a) a compound having the following formula (I):

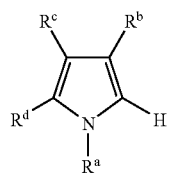

(I)

wherein
$R^a$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^a$ can join $R^d$ to form a $C_4$–$C_7$ ring;
$R^b$, $R^c$ and $R^d$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^b$, $R^c$, and $R^d$ form one or more $C_4$–$C_7$ rings, optionally containing O, S, N, P or Si atoms, that can bear substituents;
b) a Lewis acid of formula (II):

$MtR^1_3$ (II)

wherein Mt is a metal belonging to Group 13 of the Periodic Table of the Elements, $R^1$, equal to or different from each other, are halogen atoms, halogenated $C_6$–$C_{20}$ aryl or halogenated $C_7$–$C_{20}$ alkylaryl groups; two $R^1$ groups can also form with the metal Mt one condensed ring; and
c) optionally a compound of formula $KR^f_3$ wherein K is a nitrogen (N) or phosphorous (P) atom; $R^f$, equal to or different from each other, are linear or branched, saturated or unsaturated, $C_1$–$C_{30}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two $R^f$ can form one $C_4$–$C_7$ ring, optionally containing O, S, N, P or Si atoms, that can bear substituents.

16. The catalyst system according to claim 15 further comprising an alkylating agent.

17. The catalyst system according to claim 15 wherein the organometallic compound B) is chosen from the following formulae (III), (V), (IV), (VI), (VII), (IX), (VIII) or (X):

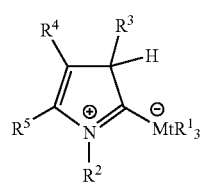

(III)

wherein
Mt is a metal belonging to Group 13 of the Periodic Table of the Elements (IUPAC); $R^1$, equal to or different from each other, are halogen atoms, halogenated $C_6$–$C_{20}$ aryl or halogenated $C_7$–$C_{20}$ alkylaryl groups; or two $R^1$ groups can form with the metal Mt one condensed ring; the substituents $R^5$, $R^4$ and $R^3$ equal to or different from each other, are hydrogen atoms, halogen atoms, linear or branched, saturated or unsaturated $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^3$, $R^4$ and $R^5$ form one or more $C_4$–$C_7$ rings, optionally containing O, S, N, P or Si;
$R^2$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms or $R^2$ can join $R^5$ to form a $C_4$–$C_7$ ring;

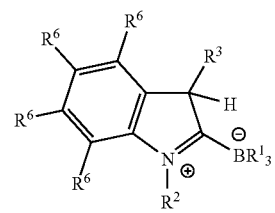

(V)

wherein
B is a boron atom; the substituents $R^6$, the same or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups optionally containing O, S, N, P, Si or halogen atoms, or two or more adjacent substituents $R^6$ form one or more $C_4$–$C_7$, optionally containing O, S, N, P or Si atoms rings that can bear substituents;

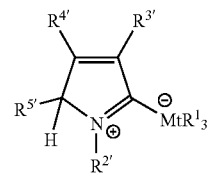

(IV)

wherein
the substituents $R^{3'}$, $R^{4'}$ and $R^{5'}$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^{3'}$, $R^{4'}$ and $R^{5'}$ form one or more $C_4$–$C_7$ rings, optionally containing O, S, N, P or Si atoms, that can bear substituents; said rings can be aliphatic and optionally contain double bonds; with the proviso that said rings are not aromatic;
$R^{2'}$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^{2'}$ can join $R^{5'}$ to form a $C_4$–$C_7$ ring;

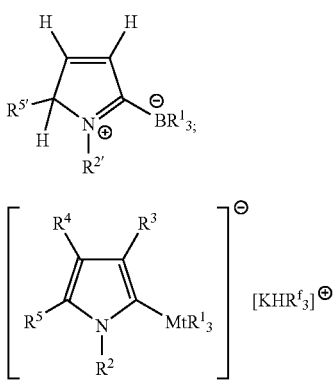
(VI)

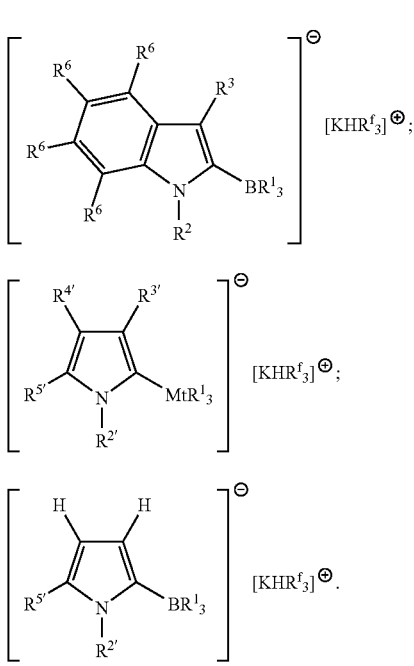
(VII)

wherein K is a nitrogen (N) or phosphorous (P) atom; $R^f$, equal to or different from each other, are linear or branched, saturated or unsaturated, $C_1$–$C_{30}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two $R^f$ can form one $C_4$–$C_7$ ring, optionally containing O, S, N, P or Si atoms, that can bear substituents;

(IX)

(VIII)

(X)

18. The catalyst system according to claim 15 wherein the transition metal organometallic compound is a metallocene compounds belonging to the following formula (XI):

$$(Cp)(ZR^7_m)_n(A)_rML_p \qquad (XI)$$

wherein $(ZR^7_m)_n$ is a divalent group bridging Cp and A; Z being C, Si, Ge, N or P, and the $R^7$ groups, equal to or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups or two $R^7$ can form a aliphatic or aromatic $C_4$–$C_7$ ring;

Cp is a substituted or unsubstituted cyclopentadienyl group, optionally condensed to one or more substituted or unsubstituted, saturated, unsaturated or aromatic rings, containing from 4 to 6 carbon atoms, and optionally containing at least one heteroatom;

A is O, S, $NR^8$, or $PR^8$ wherein $R^8$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp;

M is a transition metal belonging to group 4, 5 or to the lanthanide or actinide groups of the Periodic Table of the Elements;

the substituents L, equal to or different from each other, are monoanionic sigma ligands selected from the group consisting of hydrogen atoms, halogen atoms, $R^9$, $OR^9$, $OCOR^9$, $SR^9$, $NR^9_2$ and $PR^9_2$, wherein $R^9$ is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group, optionally containing one or more Si or Ge atoms;

m is 1 when Z is N or P, and it is 2 when Z is C, Si or Ge;

n is an integer ranging from 0 to 4;

r is 0, 1 or 2; n is 0 when r is 0;

p is an integer equal to the oxidation state of the metal M minus r+1.

19. The catalyst system according to claim 15 wherein the transition metal organometallic compound is a late transition metal complex of formula (XII) or (XIII):

$$L^aM^aX^a_p^a \qquad (XII)$$

$$L^aM^aA^a \qquad (XIII)$$

wherein $M^a$ is a metal belonging to Group 8, 9, 10 or 11 of the Periodic Table of the Elements;

$L^a$ is a bidentate or tridentate ligand of formula (XIV):

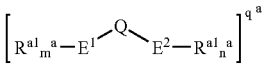
(XIV)

wherein:

Q is a $C_1$–$C_{50}$ bridging group linking $E^1$ and $E^2$, optionally containing at least one atom belonging to Groups 13–17 of the Periodic Table;

$E^1$ and $E^2$, equal to the same or different from each other, are elements belonging to Group 15 or 16 of the Periodic Table and are bonded to said metal $M^a$;

the substituents $R^{a1}$, equal to or different from each other, are selected from the group consisting of hydrogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing at least one atom belonging to groups 13–17 of the Periodic Table of the Elements; or two $R^{a1}$ substituents attached to the same atom $E^1$ or $E^2$ form a saturated, unsaturated or aromatic $C_4$–$C_7$ ring, having from 4 to 20 carbon atoms;

$m^a$ and $n^a$ are independently 0, 1 or 2, depending on the valence of $E^1$ and $E^2$, so to satisfy the valence number of $E^1$ and $E^2$; $q^a$ is the charge of the bidentate or tridentate ligand so that the oxidation state of $M^aX^a_pX^{a'}_s$ or $M^aA^a$ is satisfied, and the compound (XII) or (XIII) is overall neutral;

$X^a$, equal to or different from each other, are monoanionic sigma ligands selected from the group consisting of hydrogen, halogen, $R^a$, $OR^a$, $OSO_2CF_3$, $OCOR^a$, $SR^a$, $-NR^a_2$ and $PR^a_2$ groups, wherein the $R^a$ substituents are linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radicals, optionally containing one or more atoms belonging to groups 13–17 of the Periodic Table of the Elements; or two $X^a$ groups form a metallacycle ring containing from 3 to 20 carbon atoms;

$p^a$ is an integer ranging from 0 to 3, so that the final compound (XII) or (XIII) is overall neutral; and $A^a$ is a π-allyl or a π-benzyl group.

20. A process for the polymerization of at least one olefin comprising contacting at least one olefin under polymerization conditions with a catalyst system, comprising the product obtained by contacting:

(A) at least one transition metal organometallic compound; and (B) an organometallic compound obtained by contacting:

a) a compound having the following formula (I):

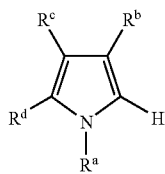

(I)

wherein $R^a$ is a linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl group, optionally containing O, S, N, P, Si or halogen atoms; or $R^a$ can join $R^d$ to form a $C_4$–$C_7$ ring;

$R^b$, $R^c$ and $R^d$, equal to or different from each other, are hydrogen atoms, halogen atoms, linear or branched, saturated or unsaturated, $C_1$–$C_{10}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two or more adjacent substituents $R^b$, $R^c$, and $R^d$ form one or more $C_4$–$C_7$ rings, optionally containing O, S, N, P or Si atoms, that can bear substituents;

b) a Lewis acid of formula (II):

$$MtR^1_3 \qquad (II)$$

wherein Mt is a metal belonging to Group 13 of the Periodic Table of the Elements; $R^1$, equal to or different from each other, are halogen atoms, halogenated $C_6$–$C_{20}$ aryl or halogenated $C_7$–$C_{20}$ alkylaryl groups; two $R^1$ groups can also form with the metal Mt one condensed ring; and c) optionally a compound of formula $KR^f_3$ wherein K is a nitrogen (N) or phosphorous (P) atom; $R^f$, equal to or different from each other, are linear or branched, saturated or unsaturated, $C_1$–$C_{30}$ alkyl, $C_6$–$C_{20}$ aryl, $C_7$–$C_{20}$ arylalkyl or $C_7$–$C_{20}$ alkylaryl groups, optionally containing O, S, N, P, Si or halogen atoms, or two $R^f$ can form one $C_4$–$C_7$ ring, optionally containing O, S, N, P or Si atoms, that can bear substituents.

* * * * *

UNITED STATES PATENT AND TRADEMARK OFFICE
CERTIFICATE OF CORRECTION

| | | |
|---|---|---|
| PATENT NO. | : 7,314,903 B2 | Page 1 of 1 |
| APPLICATION NO. | : 10/520565 | |
| DATED | : January 1, 2008 | |
| INVENTOR(S) | : Luigi Resconi et al. | |

It is certified that error appears in the above-identified patent and that said Letters Patent is hereby corrected as shown below:

At col. 24, line 6, delete "$C_7$-$C_{10}$" and insert instead --$C_7$-$C_{20}$--

At col. 28, line 47, delete "the same"

At col. 28, line 64, delete "$M_a X^a_p X^{a'}_s$," and insert instead --$M^a X^a_p X^{a'}_s$--

Signed and Sealed this

Sixteenth Day of December, 2008

JON W. DUDAS
*Director of the United States Patent and Trademark Office*